Nov. 8, 1949. R. S. MOORE Plant Pat. 893
CLIMBING MULTIFLORA POLYANTHA ROSE PLANT
Filed June 22, 1948
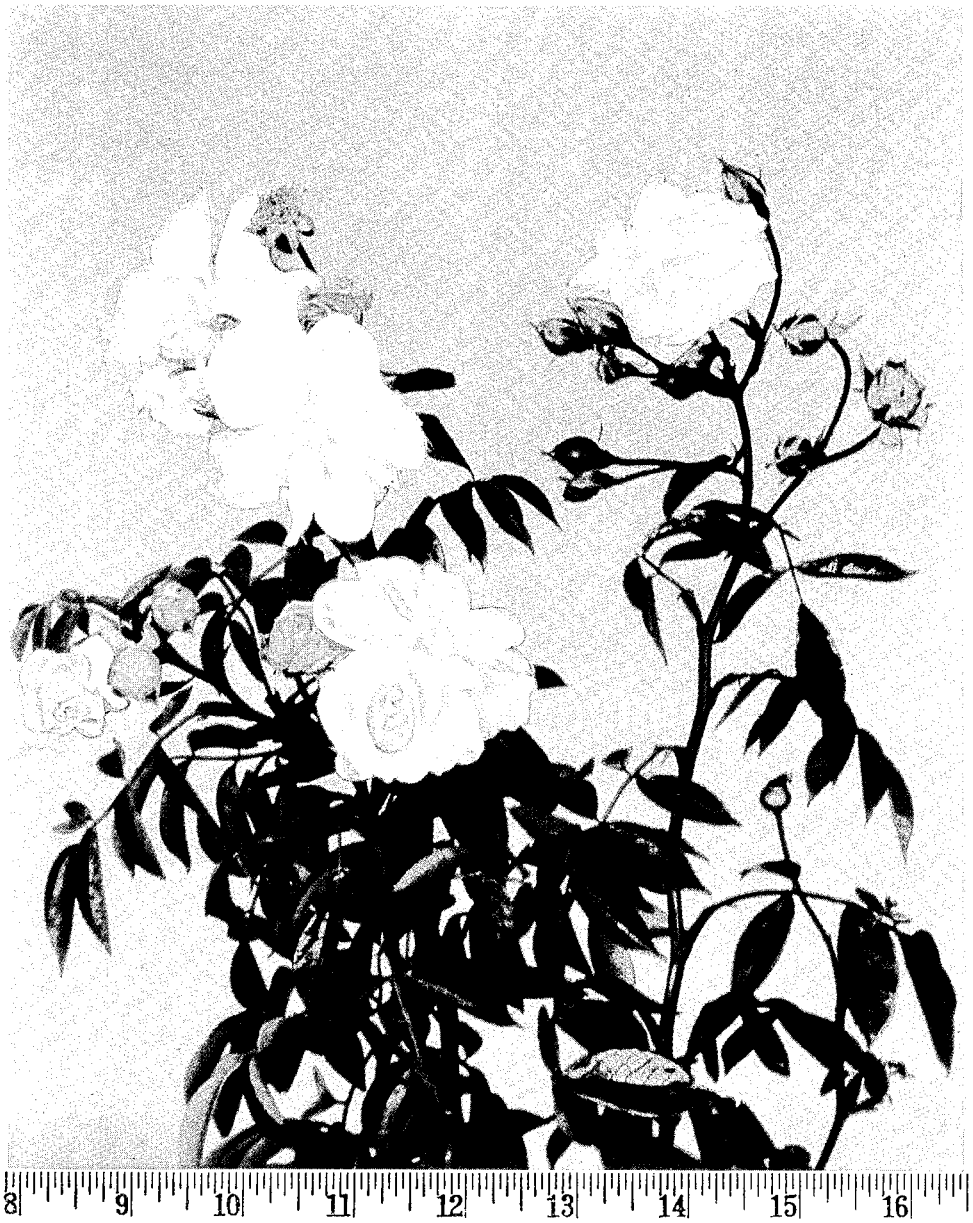
Inventor
R. S. Moore
By Robb & Robb
Attorneys Patented Nov. 8, 1949

Plant Pat. 893

UNITED STATES PATENT OFFICE

893

CLIMBING MULTIFLORA POLYANTHA ROSE PLANT

Ralph S. Moore, Visalia, Calif.

Application June 22, 1948, Serial No. 34,392

1 Claim. (Cl. 47—61)

The present invention relates to a new and distinct variety of climbing multiflora polyantha rose plant, resulting from a cross of "Etoile Luisant" and "Sierra Snowstorm," and particularly adapted for both cut flowers and garden decoration purposes.

This new variety is characterized as to novelty by a number of distinctive features, among which may be noted the following:

(1) The habit of blooming in both terminal and lateral clusters in extreme profusion in spring and early summer, followed by blooms in clusters intermittently and less heavily throughout the remainder of the growing season.

(2) Individual flowers combining the attractive form of the seed parent with the climbing trait of the pollen parent and in a shade of pink varying from the colors herein described and illustrated to lighter and softer shades of pink at the peak of bloom and throughout the remainder of the growing season.

(3) Stems and canes with an almost complete absence of prickles, sufficiently so that the prickles are difficult to find even with a systematic search.

(4) Individual buds with form similar to the dwarf "Pinkie," Plant Patent No. 712, suitable for florists' use, particularly in making up corsages.

(5) A somewhat elusive fragrance in the flowers that is very strong at times for flowers of the Polyantha type and at other times only moderate.

(6) Relatively small but abundant foliage, glossy and somewhat leathery with more than average resistance to mildew.

Comparing this new variety with its seed parent, the points of distinction are that while "Etoile Luisant" is a dwarf rose, noticeably susceptible to mildew and produces flowers of Scarlet Red, shaded Coppery, the present variety is a climber, strongly resistant to mildew and bears flowers of pink color.

Similarly, this variety differs from its pollen parent in that the flowers of "Sierra Snowstorm" are Cream and Yellow, are single, and foliage large in size, while this new variety bears pink double flowers with upwards of 38 petals, and has typically small foliage.

Asexual reproduction shows that the characteristics hold true through succeeding propagations.

In the accompanying illustration, specimens of this new variety are shown at different stages of development, exemplifying the characteristics described hereinafter.

The following is a detailed description of the new variety, all reference to color being in accordance with the Robert F. Wilson's Horticultural Colour Chart, except where indicated to be in accordance with Ridgway's Color Standards and Nomenclature:

Type: Climbing; outdoor; seedling; for cut flowers and garden decoration.

Class: Hybrid multiflora polyantha.

Breeding: Seedling.

*Seed parent.*—"Etoile Luisant" (unpatented).

*Pollen parent.*—"Sierra Snowstorm" (unpatented).

Propagation: Holds its distinguishing characteristics through succeeding propagations by budding, the only method tried so far.

*Flower*

Locality where grown: Ontario, California.

Flowers borne: Sometimes singly but usually three to five to stem; in irregular cluster; on normal stems.

Quantity of bloom: Abundant particularly in spring outdoors.

Continuity: Continuous during growing season.

Fragrance: Moderate to strong; spicy.

Bud:

*Peduncle.*—Short; slender to average caliper; bending; numerous gland-tipped cilia and numerous hairs. *Color.*—Pod Green, Plate o61, page 120, overlaid with Morocco Red, Plate I (Ridgway), particularly on side exposed to the sun.

*Before calyx breaks.*—*Size*—medium for polyantha type. *Form*—medium length; ovoid; with tomentum and gland-tipped cilia on the surface of the bud; with slender, very slightly cut foliaceous parts extending beyond the tip of the bud equal to ¼ of its length.

*As calyx breaks.*—*Color*—China Rose, Plate o24, page 111. *Sepals*—inner surface, with woolly tomentum: margins lined with stipitate glands unless adjacent sepals cover margin, then only woolly tomentum is found on margin covered. *Color*—inside: Pod Green Plate o61/2, page 120; outside: Pod Green, Plate o61/1, page 120, blotched with Morocco Red, Plate I, (Ridgway).

*As first petal opens.*—*Size*—average. Form—medium length; pointed to urn-shaped, formed somewhat like that of "Pinkie." *Color*—outside: Base Canary Yellow, Plate 2/3, page 2, with upper three-fourths of petal between Rose Madder, Plate 23/1, page 23, and Rose Madder, Plate 23/2, page 23; inside: Base Sulphur Yellow, Plate 1/3, page 1, with upper three-fourths of petal near Neyron Rose, Plate 623/1, page 76.

*Opening.*—Opens up well. Is not retarded by hot, wet or dry weather.

Bloom: Size when fully open, average; 2¼ inches to 2½ inches.

*Petalage.*—Double; from 38 to 45 petals, plus 4 to 7 petaloids arranged irregularly.

*Form.*—Flat, high centered at first; becoming very flat; petals remaining at first somewhat loosely flat with tips reflexed; becoming later at maturity more loosely with tips reflexed and slightly rolled outward.

Petals:

*Texture.*—Medium thick; with inside slightly satiny and outside slightly shiny to satiny.

*Shape.*—Outside—broadly cuneate with apex flat, with apical point usually depressed with one notch. Intermediate—cuneate with apex rounded to flat. Inside—oblanceolate with apex rounded.

*Color.*—Colors may be modified by being blotched, overlaid with other colors.

This description of a newly opened flower was made from a rose grown outdoors in the month of April, at Ontario, California:

*Color.*—*Outside petal*—outside surface: base Sulphur Yellow, Plate 1/3, page 1, with upper three-fourths of petal Rose Madder, Plate 23/3, page 23; inside surface: base Canary Yellow, Plate 2/3, page 2, with upper three-fourths of petal Fuchsine Pink, Plate 627/3, page 78. *Intermediate petal*—Outside surface: base Canary Yellow, Plate 2/3, page 2, with upper three-fourths of petal Rose Bengal, Plate 25/3, page 25; inside surface; base Canary Yellow, Plate 2/3, page 2, with upper three-fourths of petal Phlox Pink, Plate 625/3, page 77. *Inner petal*—outside surface: base Canary Yellow, Plate 2/3, page 2, with upper three-fourths of petal Rose Bengal, Plate 25/2, page 25; inside surface: base Canary Yellow, Plate 2/3, page 2, with upper three-fourths of petal Phlox Pink, Plate 625/2, page 77.

This description was made from a rose that was open for three days outdoors in the month of April, at Ontario, California:

*Color.*—*Outside petal*—outside surface: base near Sulphur Yellow, Plate 1/3, page 1, with upper three-fourths of petal Mallow Purple, Plate 630/3, page 79; inside surface—base near Sulphur Yellow, Plate 1/3, page 1, with upper three-fourths of petal Rhodamine Pink, Plate 527/3, page 138. *Inside petal*—outside surface: base near Sulphur Yellow, Plate 1/3, page 1, with upper three-fourths of petal Mallow Purple, Plate 630/3, page 79; inside surface: base near Sulphur Yellow, Plate 1/3, page 1, with upper three-fourths of petal Rhodamine Pink, Plate 527/3, page 138.

*General color effect.*—Newly opened flower—Phlox Pink, Plate 625/3, page 77. Three days open—Rhodamine Pink, Plate 527/3, page 138.

*Behavior.*—Slightly persistent, fading from Phlox Pink, Plate 625/3, page 77, to Rhodamine Pink, Plate 527/3, page 138.

*Flower longevity.*—On bush in garden—4 to 5 days in April. Cut roses grown outdoors kept at living-room temperatures—3 to 4 days in April.

*Reproductive organs*

Stamens: Average number; arranged irregularly about pistils, a few mixed with petaloids.

Filaments: Medium length; ½ to 1 cm. in length. *Color*—Sap Green, Plate 62/3, page 62. Most with anthers.

Anthers: Medium size; all open at once approximately. *Color*—upper side: center of anther near Primrose Yellow, Plate 601/3, page 65, with margins Maize Yellow, Plate 607, page 69; under side—center of anther near Primrose Yellow, Plate 601/3, page 65, with margins Maize Yellow, Plate 607, page 69.

Pollen: Moderate. *Color*—Maize Yellow, Plate 607, page 69.

Pistils: Average number; approximately 24 in number.

Styles: Moderately even to average length; average caliper; somewhat tightly bunched. *Color*—Chartreuse Green, Plate 663/3, page 90.

Stigma: *Color*—Grayish white, somewhat translucent.

Ovaries: Usually all enclosed in calyx.

Hips: Small, round; globular; somewhat like that of *Rosa setigera*. *Color*—between Currant Red, Plate 821/1, page 167, and Oxblood Red, Plate oo823/3, page 191. Moderately smooth; glandular; stipitate glands particularly at base and top of hips.

Sepals: Deciduous.

Seeds: Average number for polyantha; medium size; 2 to 4 in number.

*Plant*

Foliage:

*Leaves.*—Compound of usually 7 leaflets; very abundant; small to medium in size; heavy to somewhat leathery and glossy.

*Leaflets.*—Shape—narrowly ovate-lanceolate with apex acute; base obtuse; margin simply serrate.

*Color.*—*Mature*—upper surface: between Spinach Green, Plate o960, page 187, and Parsley Green, Plate oo962, page 193; under surface: between Spinach Green, Plate o960/3, page 187, and Willow Green, Plate ooo862, page 199. *Young*—upper surface: near Fern Green, Plate o862, page 186; under surface: between Spinach Green, Plate o960, page 187, and Parsley Green, Plate oo962, page 193.

*Rachis.*—Average size. Upper side—grooved; hairy; under side—moderately smooth; hairy; and with stipitate glands.

*Stipules.*—Medium length to long; moderately narrow with medium-length points turning out at an angle of less than 45°, reflexed downward.

*Disease.*—More than average resistant to mildew.

Growth:

*Habit.*—Climbing; much branched.

*Growth.*—Vigorous.

*Canes.*—Medium caliper to heavy.

*Main stems.*—Color—near Lavender Green, Plate ooo761/1, page 196, overlaid with Morocco Red, Plate I (Ridgeway), particularly on side exposed to the sun. *Large prickles*—none. *Small prickles and hairs*—none.

*Branches.*—Color—Scheeles Green, Plate 860/3, page 175, overlaid with Morocco Red, Plate I (Ridgeway), particularly on side exposed to the sun. *Large prickles*—none. *Small prickles*—very few. Color—near Blackish Brown (1), Plate XLV (Ridgeway). *Hairs*—none.

*New shoots.*—Color—Pod Green, Plate o61/1, page 120, slightly overlaid with Morocco Red, Plate I (Ridgeway). *Large prickles*—none. *Small prickles*—none, but some stipitate glands. *Hairs*—many.

I claim:

A new and distinct variety of hybrid, multiflora polyantha rose plant, characterized as to novelty by its prolific habit of blooming in terminal and lateral clusters in spring and early summer followed by blooms in clusters intermittently and less heavily during remainder of growing season; by its climbing habit; the form and pink shade of its individual flowers progressively varying to lighter and softer shades of pink at the peak of bloom and throughout the remainder of the growing season; the almost complete absence of prickles on its stems and canes, difficult to find even with systematic search; the form of the individual buds particularly adapted to use for corsages; the elusive fragrance of the flowers, very strong at times for polyanthas and at other times only moderate; and by the relatively small but abundant foliage, glossy and somewhat leathery with more than average resistance to mildew, substantially as shown and described.

RALPH S. MOORE.

No references cited.